US008939012B2

(12) United States Patent
Kishi et al.

(10) Patent No.: US 8,939,012 B2
(45) Date of Patent: Jan. 27, 2015

(54) THERMAL CONDUCTIVITY DETECTOR AND GAS CHROMATOGRAPH USING SAME

(75) Inventors: Naoki Kishi, Musashino (JP); Hitoshi Hara, Musashino (JP); Tetsuya Watanabe, Musashino (JP); Kentaro Suzuki, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 361 days.

(21) Appl. No.: 13/211,753

(22) Filed: Aug. 17, 2011

(65) Prior Publication Data

US 2012/0042712 A1   Feb. 23, 2012

(30) Foreign Application Priority Data

Aug. 18, 2010   (JP) ................................. 2010-183022
Aug. 12, 2011   (JP) ................................. 2011-176445

(51) Int. Cl.
G01N 25/18   (2006.01)
G01N 30/66   (2006.01)
G01N 27/18   (2006.01)

(52) U.S. Cl.
CPC ................ *G01N 30/66* (2013.01); *G01N 27/18* (2013.01)
USPC .................... 73/25.03; 73/204.23; 73/204.25; 73/204.26; 374/43; 374/44

(58) Field of Classification Search
USPC ............ 73/23.2, 23.35, 25.03, 204.23, 25.01, 73/25.05, 204.25, 204.26; 374/44, 43, 45, 374/55, 208; 422/95
See application file for complete search history.

(56) References Cited

U.S. PATENT DOCUMENTS

| 4,902,138 | A | * | 2/1990 | Goeldner et al. ................ 374/44 |
| 5,295,389 | A | * | 3/1994 | Nagata et al. ................. 73/25.03 |
| 5,377,527 | A | * | 1/1995 | Kamiunten .................... 73/25.03 |
| 5,533,412 | A | * | 7/1996 | Jerman et al. .............. 73/861.95 |
| 6,896,406 | B2 | * | 5/2005 | Gellert ............................. 374/44 |
| 7,452,126 | B2 | * | 11/2008 | Arndt et al. ...................... 374/44 |

(Continued)

FOREIGN PATENT DOCUMENTS

| JP | 59-079149 A | 5/1984 |
| JP | 11-118749 A | 4/1999 |

OTHER PUBLICATIONS

Dziuban et al., Portable gas chromatograph with intergrated components, Science Direct, Apr. 8, 2004.*

(Continued)

*Primary Examiner* — Hezron E Williams
*Assistant Examiner* — Hoang Nguyen
(74) *Attorney, Agent, or Firm* — Sughrue Mion, PLLC

(57) ABSTRACT

The present invention provides a thermal conductivity detector capable of realizing high detection performance even with the use of a miniaturized heating element, and expanding an effective applicable temperature range of a heating element, and to provide a gas chromatograph using the same. The thermal conductivity detector comprises a flow-path through which a measurement gas is caused to flow, a heating element disposed inside the flow-path, the heating element being formed on the substrate, for detecting thermal conductivity of the measurement gas according to magnitude of an amount of heat taken away from the heating element by the measurement gas, wherein said heating element is provided with a beam including a part where the beam is folded at a predetermined angle, the part being formed at the central part of the beam.

13 Claims, 8 Drawing Sheets

(56) References Cited

U.S. PATENT DOCUMENTS

| | | |
|---|---|---|
| 7,878,056 B2 * | 2/2011 | Huang et al. ............... 73/204.26 |
| 2004/0136435 A1 | 7/2004 | Gellert |
| 2004/0250601 A1 * | 12/2004 | Lin .............................. 73/25.03 |
| 2008/0108494 A1 * | 5/2008 | Han et al. ...................... 501/133 |
| 2009/0016403 A1 * | 1/2009 | Chen et al. ...................... 374/45 |

OTHER PUBLICATIONS

European Search Report for corresponding Application No. 11177935.1 issued Feb. 17, 2012.

Gokeler, Ulrich "Single Analyzer Module Process Gas Chromatograph", Siemens Applied Automation, pp. 49-58.

Lysko, Jan M. et al., "Gas micro-flow-metering with the in-channel Pt resistors", Journal of Telecommunications and Information Technology, pp. 98-100.

Lysko, Jan M. et al., "Silicon thermal conductivity detector (TCD) with the Pt resistors", Optoelectronic and Electronic Sensors V, pp. 258-261.

Dziuban, J.A. et al., "Portable gas chromatograph with integrated components" Science Direct, pp. 318-330.

* cited by examiner

Conventional

Conventional

Conventional

THERMAL CONDUCTIVITY DETECTOR AND GAS CHROMATOGRAPH USING SAME

This application claims multiple priorities from Japanese Patent Application No. 2010-183022, filed on Aug. 18, 2010, and Japanese Patent Application No. 2011-176445, filed on Aug. 12, 2011, the entire contents of which are herein incorporated by reference.

BACKGROUND

1. Technical Field

The present invention relates to a thermal conductivity detector, more specifically relates to a thermal conductivity detector capable of realizing high detection performance even with the use of a miniaturized heating element, and expanding an effective applicable temperature range of a heating element, and to relates to a gas chromatograph using the same.

A thermal conductivity detector (TCD) has been in use as the most versatile detector of a gas chromatograph. In the case of the gas chromatograph, a carrier gas such as He, $H_2$, $N_2$, Ar, and so forth is caused to flow thereto, and a measurement gas, as weighed, is introduced thereto to pass through a column, thereby splitting the measurement gas into its components over time to be measured by the detector. Qualitative analysis is conducted on the basis of an occurrence time of an output peak, and quantitative analysis is conducted on the basis of a peak area. The thermal conductivity detector converts a difference in thermal conductivity between a gas component, split off in the column, and a reference gas identical in species to the carrier gas, into an electric signal, thereby detecting respective gas components as split off, and concentration thereof.

2. Related Art

FIG. 6 is a block diagram showing a principle underlying operation of a thermal conductivity detector. In FIG. 6, reference numerals 1 to 4 denote first to fourth cells, respectively; first to forth heating elements, 1a to 4a, are each housed in the first cell 1 to the fourth cell 4, respectively. A measurement gas is introduced from an introduction port 5a of the first cell 1 to flow through the respective interiors of the first cell 1, and the second cell 2 to be outputted from an output port 5b of the second cell 2 while a reference gas is introduced from an introduction port 6a of the third cell 3 to flow through the respective interiors of the third cell 3, and the fourth cell 4 to be outputted from an output port 6b of the fourth cell 6. A bridge circuit 7 is made up of the first to fourth heating elements, 1a to 4a. A predetermined current from a constant current source 8 is fed to the bridge circuit 7, thereby causing the first to fourth heating elements, 1a to 4a, to generate heat, respectively. The measurement gas takes heat away from the heating elements 1a, and 2a, respectively, and the reference gas takes heat away from the heating elements 3a, and 4a, respectively. As a result, temperature of the respective heating elements will vary due to a difference in thermal conductivity thereof, thereby causing a change in resistance value thereof, so that an unbalanced voltage occur to the bridge circuit 7. Upon a detection circuit 9 detecting the unbalanced voltage, an amount of variation in thermal conductivity of the measurement gas is measured.

FIG. 7 is a sectional block diagram showing the principal part of a conventional sensor for use in the thermal conductivity detector described as above. In FIG. 7, reference numeral 10 denotes a block made of aluminum or stainless steel. First and second through-holes, 11, 12, in parallel with each other, are formed in the block 10, and heating elements 13, 14, made up of a filament, respectively, are disposed in the first through-hole 11, and the second through-hole 12, respectively.

Further, first to fourth inner flow-paths, 15a to 15d, extended from respective flow-inlets 11a, 12a of the first through-hole 11, and the second through-hole 12, in respective directions at an angle 45° from the first through-hole 11, and the second through-hole 12, respectively, are formed, while fifth to eighth inner flow-paths, 15e to 15h, extended from respective flow-outlets lib, 12b of the first through-hole 11, and the second through-hole 12, in respective directions at an angle 45° from the first through-hole 11, and the second through-hole 12, respectively, are formed.

The inner flow-paths, 15e to 15h, are bonded with each other to form a flow-path in a shape resembling the letter W, and the flow-path W is further bonded with the first inner flow-path 15a, and the fourth inner flow-path 15d, respectively, thereby forming respective bypass flow-paths of the first through-hole 11, and the second through-hole 12, when the first through-hole 11, and the second through-hole 12 each serve as a main flow-path. Reference numeral 18a denotes a fluid inflow pipe, and 18b a fluid outflow pipe, these pipes being reinforced by reinforcing members 19a, 19b, respectively. Reference numerals 20a, 20b, 22a, 22b each denote a lead wire, and the lead wires 20a, 20b, 22a, 22b are sealed by hermetic seals 21a, 21b, 23a, 23b, respectively.

With the detector of such a configuration as described, when a predetermined fluid, such as a measurement gas, or a reference gas is fed to an introduction hole 16, a flow of the predetermined fluid passes through the introduction hole 16 to be subsequently split into two flows, and each flow proceeds through the second flow-path 15b, and the third inner flow-path 15c, respectively. Further, a flow having passed through the second inner flow-path 15b is further split into two flows, each flow moving through the first through-hole 11, and the first to fifth inner flow-paths, 15a, 15e, respectively, and subsequently, respective flows are merged with each other to form a flow, whereupon the flow moves through the sixth flow-path 15f.

A flow of the predetermined fluid, moving through the third inner flow-path 15c, is similarly, split into two flows, each flow moving through the second through-hole 12, and the fourth to eighth inner flow-paths 15d, 15h, respectively, to be subsequently merged with each other before moving through the seventh inner flow-path 15g. Further, the respective flows of the fluid, moving through the sixth inner flow-path 15f, and the seventh inner flow-path 15g, are merged with each other to be delivered outside the block 10 via a delivery hole 17.

The blocks configured as above are provided to be used for the measurement gas, and the reference gas, respectively, and an unbalanced voltage according to a difference in thermal conductivity between the measurement gas, and the reference gas is drawn out. The heating elements 13, 14, shown in FIG. 7, correspond to the heating elements 1a, 2a, in FIG. 7, respectively (to the heating elements 3a, 4a, in FIG. 6, in the case of the block through which the reference gas is circulated).

For the heating element, a filament coil with a total wire length in a range of several to several tens of cm has so far been in heavy use, however, there has lately been adopted a practice to form a miniaturized sensor of the thermal conductivity detector on a substrate with the use of the techniques of MEMS (Micro Electro Mechanical System). As a specific example, a practice has been adopted whereby flow-paths are formed in the interior between two substrates stuck with each other, and a filament is miniaturized to be formed on one of the substrates such that the filament is disposed in the space of each of the flow-paths.

FIG. 8 is a view showing an example in which a gas flow-path, and a filament are formed on a substrate by use of the MEMS techniques. In FIG. 8, reference numeral 10 denotes a silicon (Si) substrate, the silicon (Si) substrate serving as one half part of an inner wall enclosing the filament. Reference numeral 20 denotes a Pyrex (registered trademark) (Px) glass substrate, and a beam 11 extended in the direction of a line Y is formed on the Pyrex glass substrate. A Pyrex glass represents one example of borosilicate glass. The beam 11 is formed in a slender shape having a width w, and a thickness d. Regions 12, 13, spreading so as to be rectangular in shape, respectively, are disposed on the sides of respective ends of the beam 11, these regions, and the beam 11 being made of material prepared by adding an additive to silicon, and adjusted so as to cause a resistance value to be reduced. The beam 11 functions as the filament, and the regions 12, 13 each function as the electrode connected to the filament. The Pyrex glass substrate 20 positioned underneath the regions 12, 13 is provided with a through-hole (not shown), and the electrodes are taken out through this through-hole.

The Pyrex glass substrate 20 is fixedly attached to the silicon substrate 10 in such a way as to be superposed therewith from the underside in the figure by, for example, anodic bonding. A hollow part 21 is formed in the central region of the Pyrex glass substrate 20, and when the Pyrex glass substrate 20 is fixedly attached to the silicon substrate 10, the beam 11 to serve as the filament will be disposed just in the space of the hollow part 21. The hollow part 21 is adjacent to a flow-path (not shown), and heat of the filament is taken away by a gas diffusing inside the hollow part 21.

In the case where the sensor of the thermal conductivity detector is formed by use of the MEMS techniques, as described, there can be derived merits including;

because the flow-path, and the filament can be formed by a semiconductor manufacturing process, highly developed processing techniques will not be required of a worker, because a plurality of sensors can be concurrently formed in a wafer, this process is inexpensive, and suitable for mass production, since the sensor can be miniaturized, time necessary up to thermal stabilization of the sensor can be shortened, because the body of a thermal conductivity detector in whole can be miniaturized, constraints imposed on an installation location can be reduced, and it is possible to concurrently manufacture a variety of thermal conductivity detectors provided with a flow-path, and a filament, for use under various conditions differing from each other.

A thermal conductivity detector is described in the following Patent Documents 1 and 2.

PATENT DOCUMENTS (Patent Document 1) JP59-79149A
(Patent Document 2) JP11-118749A The thermal conductivity detector is an apparatus to capture a change in thermal energy released from the surface of a filament in the sensor, by conduction through a gas, as a change in thermal conductivity of the gas. Accordingly, the higher a ratio of the thermal energy released from the surface of the filament, by conduction through the gas, to total energy consumption of the filament, the more desirable.

If the case of using the filament miniaturized by use of the MEMS techniques shown in FIG. 8, as the heating element, is compared with the case of using the filament coil not relying on the MEMS techniques, a ratio of thermal energy dissipating through roots at the respective ends of the miniaturized filament will be greater as compared with that of the filament coil with the total wire length in the range of several to several tens of cm, so that sensitivity will undergo deterioration.

In order to increase thermal energy released through the intermediary of a gas, even in the case of a miniaturized filament structure, it is effective to bring the inner wall closer to the filament as much as possible, provided that the inner wall is greater in thermal conductivity than the gas by an order of magnitude. If the inner wall is brought closer to the filament such that an interval therebetween is on the order of several μm, it is possible to obtain heat characteristics equivalent to those of the conventional thermal conductivity detector using the filament coil.

However, the conventional filament miniaturized by use of the MEMS techniques occasionally undergoes buckling upon application of heat, thereby causing deformation to a large extent. If temperature of the filament rises when heat is applied thereto, internal stress will increase due to thermal expansion, and buckling distortion will occur to the filament at a certain temperature, or higher. If the filament is formed in, for example, such a shape as shown in FIG. 8, the filament will undergo buckling downward in the figure due to the application of heat thereto, and the filament as buckled will come into contact with the inner wall of the hollow part 21, so that performance of a thermal conductivity detector will be lost. For this reason, heating-applicable temperature of the filament is, in effect, limited. In order to keep the sensitivity of the sensor at a constant level, a distance between the filament, and the inner wall should not be allowed to vary to a large extent even though the filament is stopped short of coming into contact with the inner wall.

Further, the conventional filament miniaturized by use of the MEMS techniques is formed of the material prepared by adding the additive to silicon, and adjusted so as to cause a resistance value thereof to be reduced, however, the effect of noise on the conventional filament described is greater as compared with a metal filament made up of a tungsten wire, and so forth, no relying on the MEMS techniques, and there is a tendency that an S/N ratio of the conventional filament is poor.

SUMMARY OF THE INVENTION

Exemplary embodiments of the present invention address the above disadvantages and other disadvantages not described above. However, the present invention is not required to overcome the disadvantages described above, and thus, an exemplary embodiment of the present invention may not overcome any disadvantages.

It is one of illustrative aspects of the present invention to provide a thermal conductivity detector capable of realizing high detection performance even with the use of a miniaturized heating element, and expanding an effective applicable temperature range of a heating element, and to provide a gas chromatograph using the same.

According to one or more illustrative aspects of the invention, there is provided a thermal conductivity detector comprising a flow-path through which a measurement gas is caused to flow, a heating element disposed inside the flow-path, the heating element being formed on the substrate, for detecting thermal conductivity of the measurement gas according to magnitude of an amount of heat taken away from the heating element by the measurement gas, wherein said heating element is provided with a beam including a part where the beam is folded at a predetermined angle, the part being formed at the central part of the beam.

DETAILED DESCRIPTION OF EXEMPLARY EMBODIMENTS

Figure 1A:
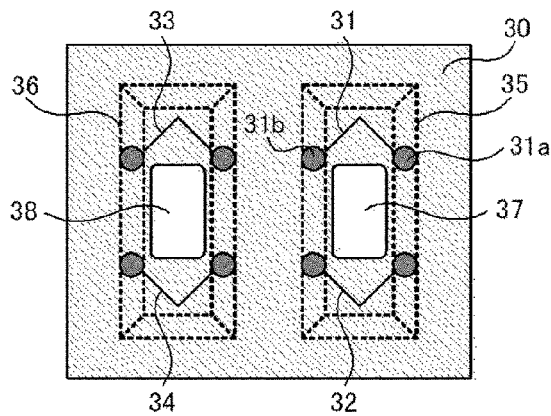
FIG. 1(A) to FIG. 1(C) are views each showing a substrate forming a sensor of the thermal conductivity detector according to the first embodiment of the invention.
Figure 1B:
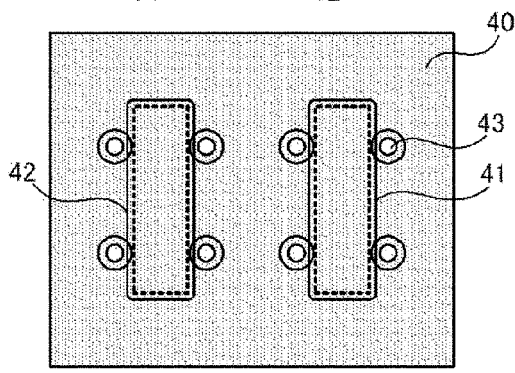
Figure 1C:
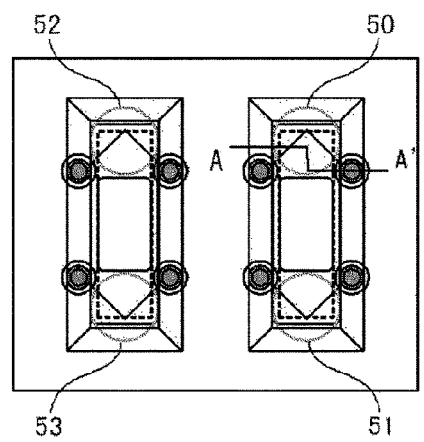

A first embodiment of a thermal conductivity detector according to the invention is described hereinafter with reference to FIGS. 1 to 4. FIG. 1(A) to FIG. 1(C) are views each showing a substrate of a sensor of the thermal conductivity detector according to the first embodiment of the invention, wherein FIG. 1(A) is a view showing a silicon substrate 30, FIG. 1(B) a view showing a Pyrex glass substrate 40, and FIG. 1(C) a view showing a state in which the Pyrex glass substrate 40 is superimposed on the silicon substrate 30. The sensor according to the present embodiment is made up by forming filaments on the silicon substrate, forming concaves to serve as flow-paths in both the silicon substrate, and the Pyrex glass substrate, and bonding these substrates with each other, thereby forming the sensor such that the flow-paths, and the filaments are positioned inside a bonded substrate.

In FIG. 1(A), filaments 31 to 34 are formed on the silicon substrate 30. Electrodes 31a, 31b, connected to the filament 31, are formed at respective ends of the filament 31, on the top-side surface of the silicon substrate 30. With each of the filaments 32 to 34, electrodes are formed at respective ends thereof, as is the case with the filament 31.

The filaments 31, 32 are formed so as to be symmetrical with each other in the vertical direction in the figure while respective positions of the filaments 31, 32, in the horizontal direction in the figure, are aligned with each other. Similarly, the filaments 33, 34, as well, are formed so as to be symmetrical with each other in the vertical direction in the figure while respective positions thereof, in the horizontal direction in the figure, are aligned with each other. Openings 37, 38 each are formed between the filaments 31, 32, and between the filaments 33, 34, respectively, the openings 37, 38 each being provided in order to secure a high ventilation characteristic between the top-side surface of the silicon substrate 30, and the rear-side surface thereof.

Figure 6:
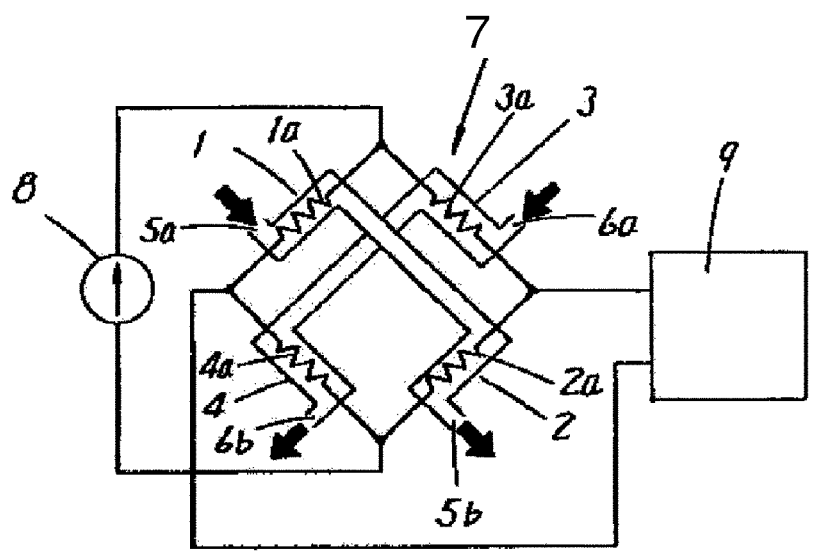
FIG. 6 is a block diagram showing a principle underlying operation of a thermal conductivity detector.
Figure 7:
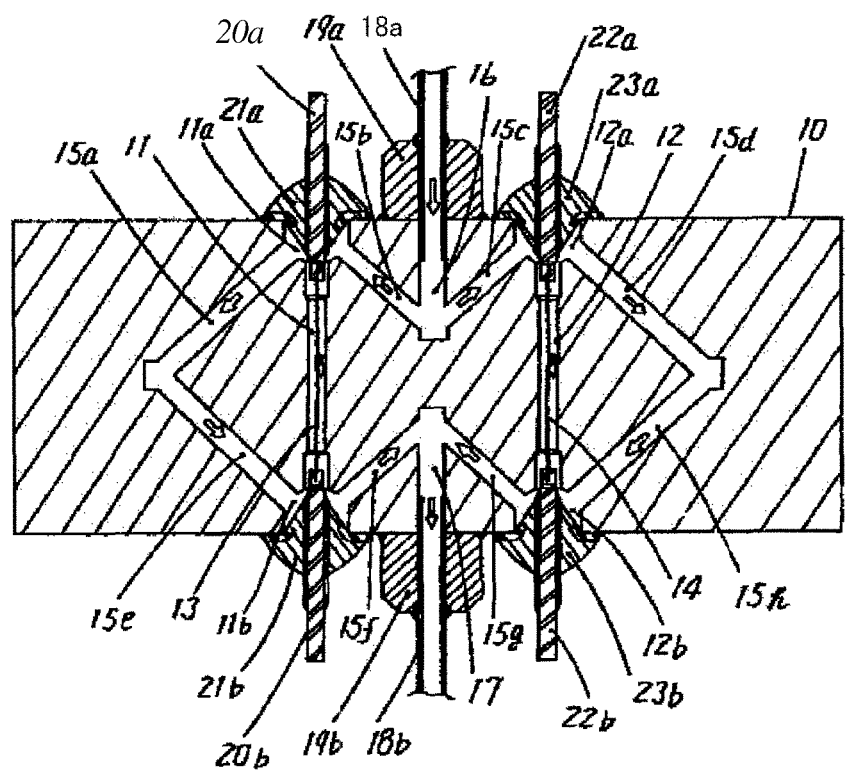
FIG. 7 is a sectional block diagram showing a principal part of a conventional sensor for use in the thermal conductivity detector.

The filaments 31, 32, and the filaments 33, 34 are a pair of filaments, respectively, to be disposed in respective flow-paths for use in circulation of the same gas, and, for example, the filaments 31, 32 correspond to filaments (the heating element) 1a, 2a, shown in FIG. 6, respectively (the filament disposed in the flow-path through which the measurement gas flows), while the filaments 33, 34 correspond to the filaments (the heating element) 3a, 4a, shown in FIG. 6, respectively (the filament disposed in the flow-path through which the reference gas flows). The bridge circuit 7 shown in FIG. 6 is made up by properly connecting the respective electrodes of the filaments 31, 32, 33, 34, with each other.

Grooves 35, 36 are formed in the rear-side surface of the silicon substrate 30. The groove 35 is formed at a position where the groove 35 overlaps filaments 31, 32 while the groove 36 is formed at a position where the groove 36 overlaps the filaments 33, 34. Upon bonding the silicon substrate 30 with the Pyrex glass substrate 40, the groove 35 functions as a flow-path through which the measurement gas is circulated to the filaments 31, 32, respectively, and the groove 36 functions as a flow-path through which the reference gas is circulated to the filaments 33, 34, respectively.

Figure 2:
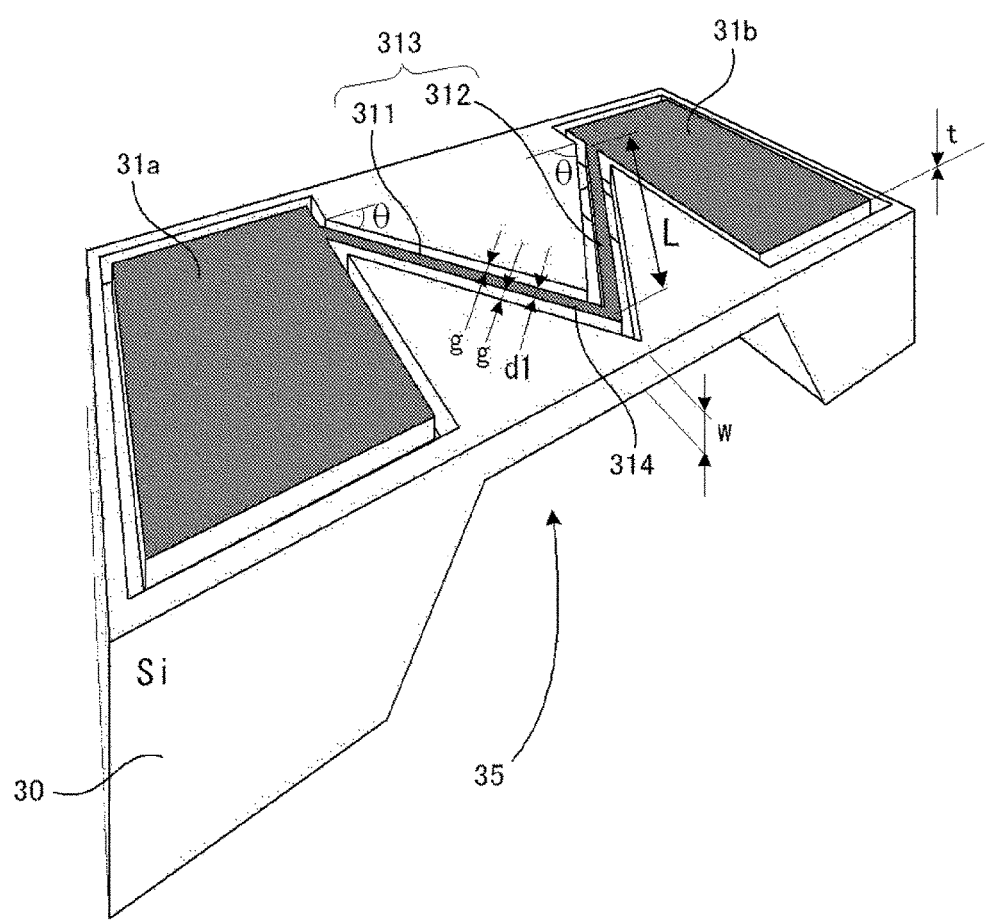
FIG. 2 is an enlarged perspective view showing a filament, and electrodes thereof, in section.

FIG. 2 is an enlarged perspective view showing a filament, and electrodes thereof, in section. As the representative of the filament, and the electrodes thereof, respectively, the filament 31, and the electrodes 31a, 31b, thereof, are described hereinafter.

The filament 31 is provided with a beam 313 and a thin metal film 314 formed on the beam 313. The beam 313 is comprised of a first beam 311, and a second beam 312. With the beam 313, the first beam 311, and the second beam 312 are each formed in such a shape as to be extended in respective directions at an initial angle θ from respective regions of the filament 31, serving as the electrodes 31a, 31b, and the beam 313 is shaped such that the other end of the first beam 311 is bonded with the other end of the second beam 312. More specifically, as shown in FIG. 2, the beam 313 is in a shape including a bonded part between the first beam 311, and the second beam 312, resembling the letter V in shape, corresponding to a folded part of the beam 313, provided at the center thereof, where the beam 313 is folded by a predetermined angle.

The first beam 311, and the second beam 312 are each formed so as to have a length L, a width d1, and a thickness w, while an air gap having a width g, reaching the groove 35, is provided in the respective peripheries of the first beam 311, and the second beam 312.

The beam 313 is formed by forming the groove 35 by applying anisotropic etching from the rear-side surface of the substrate so as to leave only the thickness w of the beam 313 out, and by applying penetration processing from the top-side surface of the substrate, by use of photolithography, and dry etching, thereby forming the beam 313 in such a shape as extended at the initial angle θ from the respective electrodes. The thin metal film 314 having a thickness t, with tungsten deposited thereon, serving as a resistor, is formed on the top-side surface of the beam 313. Further, tungsten is concurrently deposited on the regions at the respective ends of the beam 313, serving as the electrodes 31a, 31b, respectively, the electrodes 31a, 31b being rendered electrically continuous to the thin metal film 314 formed on the beam 313. That is, the thin metal film 314 is formed on the beam 313, and the thin metal film 314 is in a state where the ends thereof are connected to the electrodes 31a, 31b, in pairs, respectively.

The beam 313, and the thin metal film 314 formed thereon make up the filament 31. The beam 313 serves as a thermal structure of the filament 31, and the thin metal film 314 on the beam 313 serves as an electrical element of the filament 31.

Now, reverting to FIG. 1, description is continued hereinafter. In FIG. 1(B), grooves 41, 42 are formed in the rear-side surface of the Pyrex glass substrate 40. The grooves 41, 42 each are formed in such a shape as to cover the filaments 31, 32, and the filaments 33, 34, at a predetermine depth d2, respectively, when the Pyrex glass substrate 40 is bonded with the silicon substrate 30. When the Pyrex glass substrate 40 is bonded with the silicon substrate 30, the groove 41 functions as the flow-path through which the measurement gas is circulated, and the groove 42 functions as the flow-path through which the reference gas is circulated. Through-holes 43 numbering eight pieces in total are formed at positions located in respective peripheral regions of the grooves 41, 42, and overlying the respective electrodes on the silicon substrate 30. The grooves 41, 42, and the through-holes 43 are each formed by processing including wet etching, dry etching, sandblasting, and so forth.

The silicon substrate 30, and the Pyrex glass substrate 40 are formed in advance as described above, and subsequently, the top-side surface of the silicon substrate 30 is bonded with the rear-side surface of the Pyrex glass substrate 40 by anodic bonding. Further, since the anodic bonding can be adopted for combining these substrate materials with each other, strong bonding high in air tightness can be easily obtained.

FIG. 1(C) is a view showing a state in which the Pyrex glass substrate 40 is superimposed on the silicon substrate 30. The grooves 41, 42 of the Pyrex glass substrate 40 overlap the filaments 31, 32, and the filaments 33, 34, respectively, those filaments being provided on the silicon substrate 30. Further, the through-holes 43 of the Pyrex glass substrate 40 overlap the electrodes on the silicon substrate 30, respectively. A bonded substrate made up as above is installed on another member provided with a measurement gas introduction inlet 50 for introducing the measurement gas to the groove 35 provided in the rear-side surface of the silicon substrate 30, a measurement gas delivery outlet 51 for delivering the measurement gas from the groove 35, a reference-gas introduction inlet 52 for introducing the reference-gas to the groove 36, and a reference-gas delivery outlet 53 for delivering the reference-gas from the groove 36, thereby operating as the sensor of a thermal conductivity detector.

Figure 3:
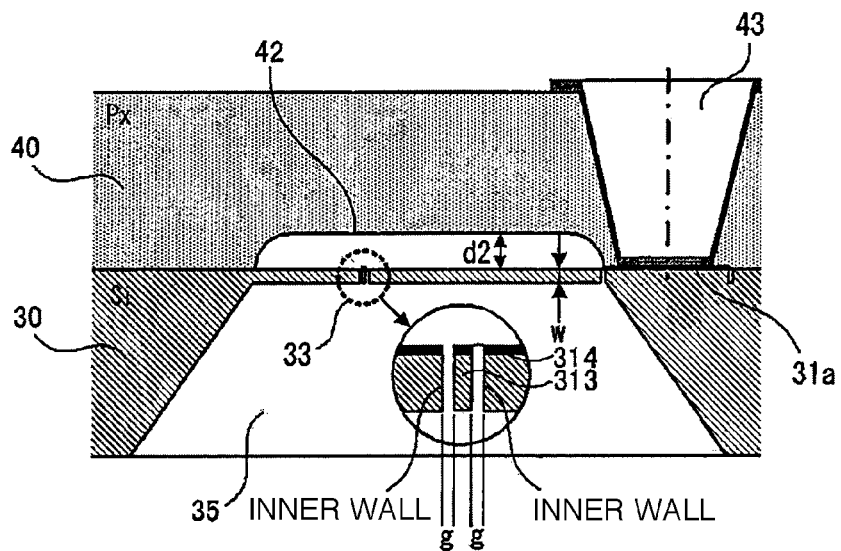
FIG. 3 shows a sectional view taken on line A-A' of FIG. 1(C)

FIG. 3 shows a sectional view taken on line A-A' of FIG. 1(C), as an example of the sectional view of the bonded substrate. Further, the filaments 32 to 34, other than the filament 31, each have a similar configuration. With the silicon substrate 30 being in such a state as bonded with the Pyrex glass substrate 40, the filament 31 is disposed in the space of a gas flow-path formed by the groove 35, and the groove 41. Metal is applied to the through-hole 43, thereby enabling a potential of the electrode to be taken out externally.

Further, if the width g of the air gap formed in the peripheral regions of the beam 313 is set to a smaller value, this will cause the inner wall of the air gap, opposing the filament 31 on the silicon substrate 30, to come into close proximity of the filament 31. By so doing, sufficient thermal energy can be released through the intermediary of a gas even in the case where the filament 31 is miniaturized as is the case with the present embodiment.

Figure 4:
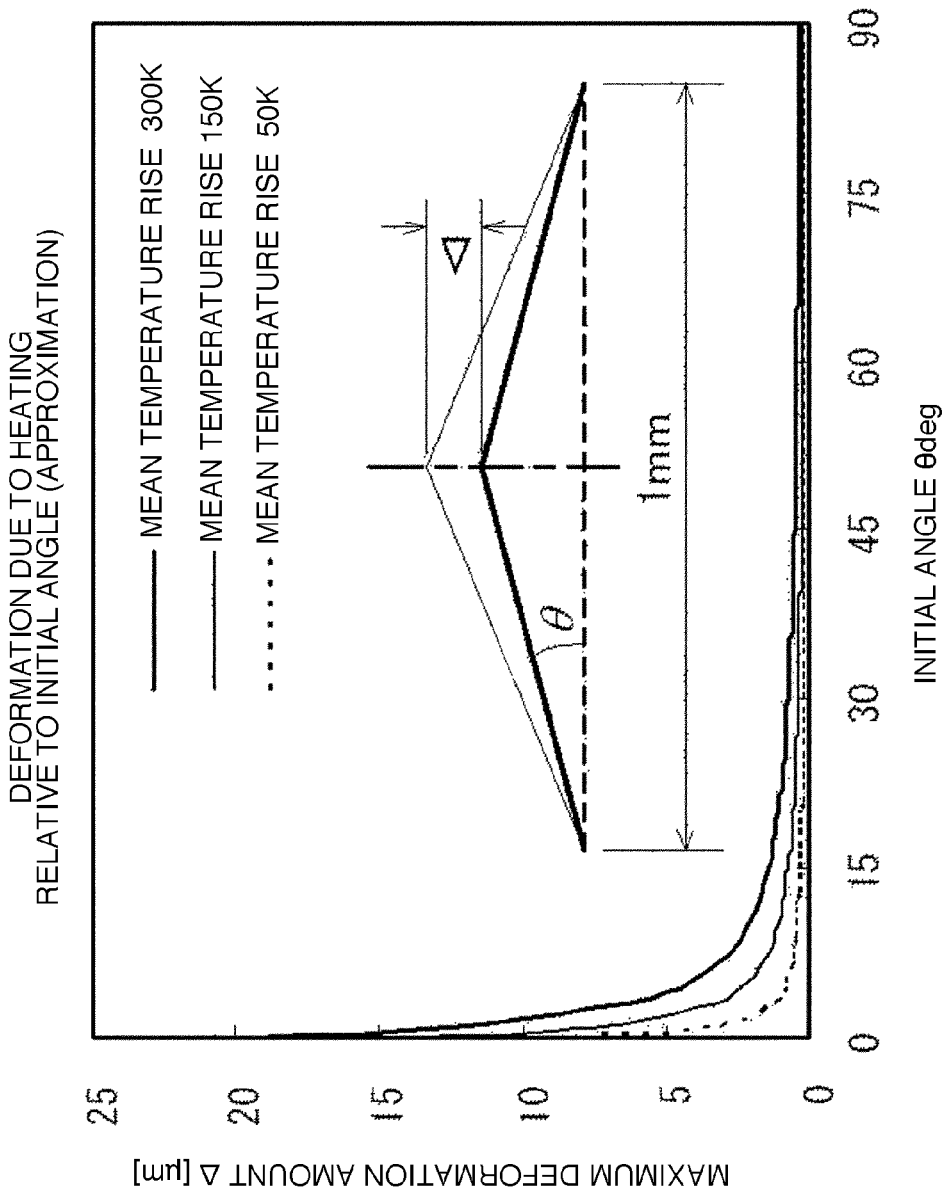
FIG. 4 is a graph showing a relationship between a maximum deformation amount A of the filament, and the initial angle θ thereof.

Now, the filament 31 undergoes deformation due to heating. FIG. 4 is a graph showing a relationship between a maximum deformation amount $\Delta$ of the filament 31, and the initial angle $\theta$, the graph being based on calculation with the use of coefficient of linear expansion of silicon on the assumption that the filament 31 is of a truss structure. The maximum deformation amount $\Delta$ represents displacement in the direction of the apex of a truss structure, corresponding to displacement in the direction of the apex of the letter "V" of the beam 313 (and displacement within the horizontal plane of the silicon substrate), in FIG. 2.

The greater a rise in temperature of the filament 31 is, the greater the maximum deformation amount $\Delta$ will be. Further, if the initial angle $\theta$ is large, the maximum deformation amount $\Delta$ is small, however, if the initial angle $\theta$ decreases (to about 15 degrees or less), the maximum deformation amount $\Delta$ will abruptly increase, and buckling occurs to the filament 31 at the initial angle $\theta \approx 0$.

Accordingly, if the beam 313 of the filament 31 is made up of the first beam 311, and the second beam 312, provided with a predetermined initial angle $\theta$, respectively, in advance (in other words, the beam 313 is formed in a shape such that the beam 313 is folded at a predetermined angle, in advance), this will control the maximum deformation amount A of the filament 31 so as to fall within a range where desired sensitivity can be obtained. In other words, if the filament 31 is provided with the initial angle $\theta$, this will enable an applicable temperature of the filament 31 without causing buckling distortion thereof to be increased, thereby expanding an effective applicable temperature range of the filament 31.

Figure 8:
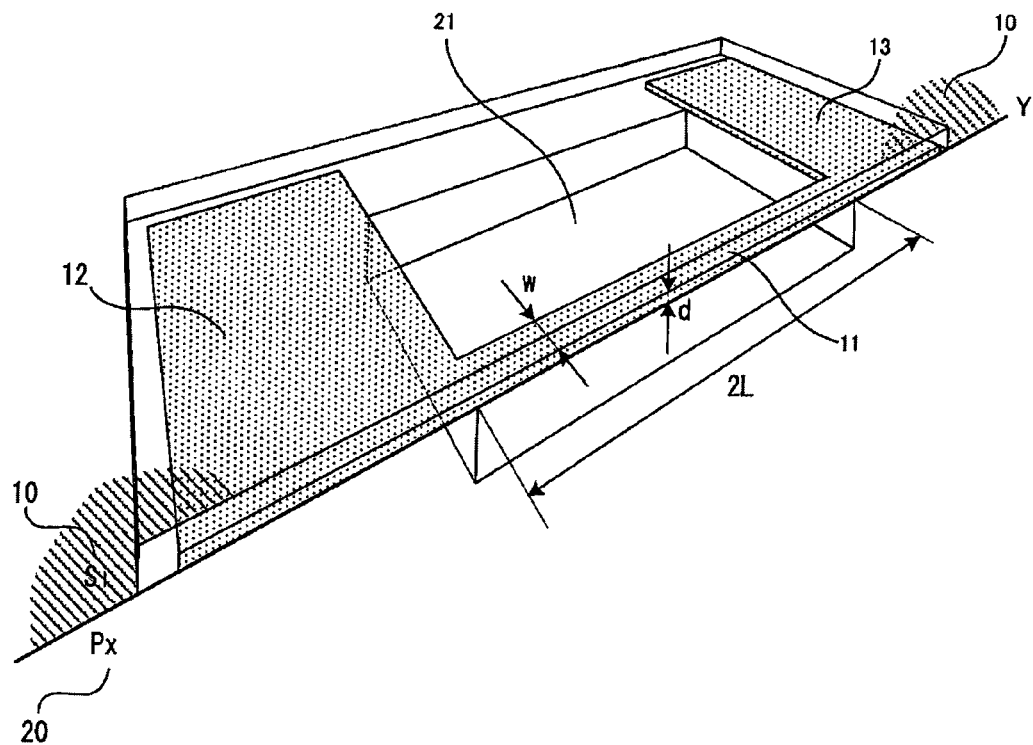
FIG. 8 is conventional gas flow-path and filament formed on a substrate with the use of MEMS techniques.

The conventional filament formed with the use of the MEMS techniques, shown in FIG. 8, corresponds to the case of the initial angle $\theta$=0 deg in FIG. 4.

A specific value of the initial angle $\theta$ is found from magnitude of a temperature rise, calculated back from an anticipated temperature applied to the filament 31, and a maximum deformation amount allowable to the filament 31.

Further, a direction of deformation that can occur to the filament 31 is not limited to within the horizontal plane of the silicon substrate 30, the direction being affected by a balance between the thickness w, and the width d1 of the beam 313. If the filament 31 is deformed in the vertical direction of the silicon substrate 30, this will cause respective areas having the width g, opposite to each other, to vary, so that sensitivity cannot be kept constant. For this reason, the balance between the thickness w, and the width d1 of the beam 313 is set such that the direction of deformation due to heating of the filament 31 is other than the vertical direction.

The thermal conductivity detector according to the first embodiment of the invention is made up as described in the foregoing, and since the filament 31 is provided with the beam 313 including the part where the beam 313 is folded at the predetermined angle, the part being formed at the central part of the beam 313, it is possible to provide a thermal conductivity detector capable of realizing high detection performance even though the filament 31 is miniaturized, and expanding the effective applicable temperature range of the filament 31.

Further, since the filament 31 is made up of the beam 313 for forming the thermal structure, and the resistor made up of another member, assuming the responsibility for providing electrical characteristics, flexibility in designing can be increased. Still further, since a silicon material that is advantageous as a thermal structure can be combined with the beam 313, and a metal having less electrical noise can be combined with the resistor, it is possible to form an ideal filament 31.

Yet further, since the filament 31 is in close proximity to the inner wall, the filament 31 is capable of causing sufficient thermal energy to be released through the intermediary of a gas even though the filament 31 is miniaturized.

Yet further, with the beam 313, at least either one of the thickness w, and the width d1 is set such that the direction of deformation due to heating of the filament 31 is within a plane horizontal with the surface of the silicon substrate 30, so that deformation of the filament 31, in the vertical direction of the silicon substrate 30, can be inhibited, thereby preventing deterioration in the sensitivity of the sensor.

Because the sensor of the thermal conductivity detector according to the present embodiment is manufactured by a semiconductor manufacturing process, it is possible to implement the respective shapes of the filaments 31 to 34, a distance between the filament, and a flow-path wall surface, and so forth, in accordance with a design, thereby enabling fabrication with high reproducibility. Further, it is possible to inhibit deformation due to heating, thereby expanding an operational temperature range.

Figure 5:
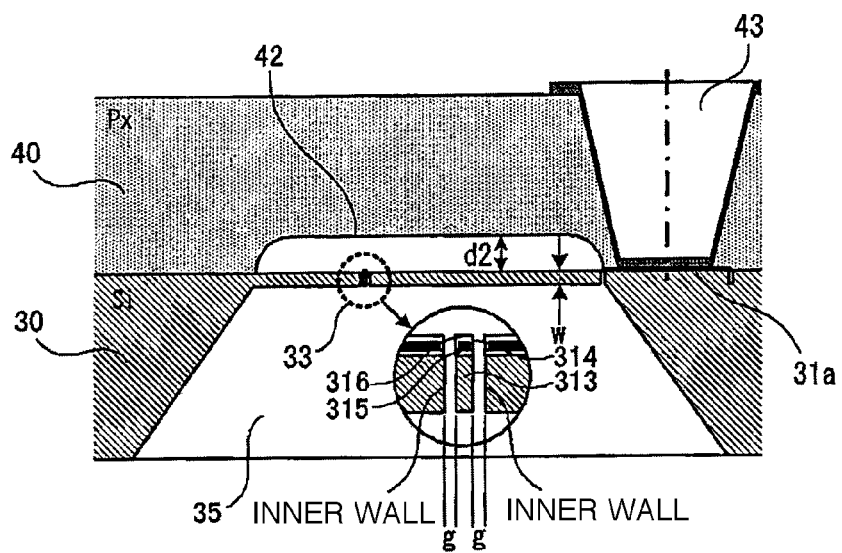
FIG. 5 shows a sectional view taken on line A-A' of FIG. 1(C) according to another example.

With the present embodiment, the thin metal film 314 is deposited directly on the beam 313 made of the silicon material, however, a thin film for preventing silification may be provided between the beam 313, and the thin metal film 314 as necessary. Further, an insulating film may be provided between the beam 313, and the thin metal film 314. Still further, an antioxidant thin film may be provided on the thin metal film 314. Furthermore, a thin film for catalysis inhibition may be provided on the thin metal film 314. There is described another example in FIG. 5 wherein a film for preventing silification (or an insulating film) 315 is provided between the beam 313, and the thin metal film 314 and an antioxidant film 316 (or a film for catalysis inhibition) 316 provided on the thin metal film 314.

Further, with the present embodiment, the silicon substrate with the filaments formed thereon is bonded with the Pyrex glass substrate, however, it is to be pointed our that constituent materials of these substrates are not limited thereto, and that other materials may be combined with each other provided that strong bonding high in air-tightness can be implemented.

If a gas chromatograph is made up by use of the thermal conductivity detector according to the present embodiment for detection of gas components, accuracy in gas detection can be enhanced.

Further, the present invention is applicable to a Pirani gauge for measuring a degree of vacuum through detection of thermal conductivity, as is the case with the gas chromatograph.

It is to be understood that the silicon substrate 30 according to the present invention corresponds to the substrate described under the heading of "What is claimed is", the filament corresponds to the heating element, and the Pyrex glass substrate 40 corresponds to the second substrate, respectively.

With the present embodiment, it is described that tungsten is a constituent material of the thin metal film 314, however, the constituent material of the thin metal film 314 may be at least one element selected from the group consisting of molybdenum, platinum, rhodium, nickel, and cobalt.

The filament coil made up of a tungsten wire is mainly used in the conventional thermal conductivity detector, and in the case where a tungsten thin film is formed on the thin metal film 314, the tungsten thin film is advantageous in that there is a high possibility of obtaining performance equivalent to that of the filament coil.

In the case where a molybdenum thin film is formed on the thin metal film 314, the molybdenum thin film is advantageous in that heat treatment for overcoming deterioration in temperature coefficient of the resistance, upon formation of the thin film, is effective at a lower temperature because molybdenum has a boiling point, and recrystallization temperature lower than those of tungsten.

In the case where a platinum thin film is formed on the thin metal film 314, the platinum thin film is advantageous in that platinum is excellent in durability such as heat resistance, gas resistance, and so forth.

In the case where a rhodium thin film is formed on the thin metal film 314, the rhodium thin film is advantageous in that rhodium is excellent in durability as is the case with platinum, and further, rhodium is high in temperature coefficient of the resistance.

In the case where a nickel thin film is formed on the thin metal film 314, the nickel thin film is advantageous in that nickel is large in temperature coefficient of the resistance except for at Curie point (around 350° C.).

In the case where a cobalt thin film is formed on the thin metal film 314, the cobalt thin film is advantageous in that cobalt is higher in Curie point (at around than 1100° C.) than nickel, and the cobalt thin film has a wider range in which the temperature coefficient of the resistance is large.

While the present invention has been shown and described with reference to certain exemplary embodiments thereof, other implementations are within the scope of the claims. It will be understood by those skilled in the art that various changes in form and details may be made therein without departing from the spirit and scope of the invention as defined by the appended claims.

What is claimed is:

1. A thermal conductivity detector comprising:
   a flow-path through which a measurement gas is caused to flow, and
   a heating element, for detecting thermal conductivity of the measurement gas according to a magnitude of an amount of heat taken away from the heating element by the measurement gas, disposed inside the flow-path, the heating element comprising of a beam, formed from a substrate, and a thin metal film formed on the beam, the ends of the thin metal film being connected with a pair of electrodes formed on the surface of the substrate, respectively,
   wherein said heating element is provided with a beam including a part where the beam is folded at a predetermined angle, the part being formed at the central part of the beam,
   wherein at least either one of a thickness, and a width of the beam is set such that a direction of deformation of the heating element, due to heating of the heating element, is within a plane horizontal with the surface of the substrate.

2. The thermal conductivity detector according to claim 1, wherein the heating element is formed such that inner walls of an air gap formed in the beam, opposite to each other, in section, come into close proximity to the heating element.

3. The thermal conductivity detector according to claim 1, wherein the substrate, and a second substrate other than the substrate are stuck with each other to form a bonded substrate, and the flow-path is made up of grooves formed in the respective substrates of the bonded substrate.

4. The thermal conductivity detector according to claim 1, wherein a constituent material of the thin metal film is at least one element selected from the group consisting of tungsten, molybdenum, platinum, rhodium, nickel and cobalt.

5. The thermal conductivity detector according to claim 1, wherein the heating element is provided with at least either of a film for preventing silification, and an insulating film, formed between the thin metal film, and the beam.

6. The thermal conductivity detector according to claim 1, wherein the heating element is provided with at least either of an antioxidant thin film, and a film for catalysis inhibition, formed on the thin metal film.

7. The thermal conductivity detector according to claim 1, wherein the substrate is a silicon substrate.

8. The thermal conductivity detector according to claim 3, wherein the second substrate is a borosilicate glass substrate.

9. A gas chromatograph comprising the thermal conductivity detector according to claim 1, wherein the thermal conductivity detector is used for detection of gas components.

10. A gas chromatograph comprising the thermal conductivity detector according to claim 1, wherein the predetermined angle of the fold is between 10 degrees and 170 degrees.

11. A gas chromatograph comprising the thermal conductivity detector according to claim 1, wherein the beam is supported only at a first and a second end.

12. A thermal conductivity detector comprising:
a flow-path through which a measurement gas is caused to flow, and
a heating element, for detecting thermal conductivity of the measurement gas according to a magnitude of an amount of heat taken away from the heating element by the measurement gas, disposed inside the flow-path, the heating element comprising of a beam, formed from a substrate, and a thin metal film formed on the beam, the ends of the thin metal film being connected with a pair of electrodes formed on the surface of the substrate, respectively,
wherein said heating element is provided with a first beam and a second beam, each having a first and a second end, wherein the first and second beam are attached to each other at the first ends at a predetermined angle, such that the beams are not parallel,
wherein at least either one of a thickness, and a width of the beam is set such that a direction of deformation of the heating element, due to heating of the heating element, is within a plane horizontal with the surface of the substrate.

13. A gas chromatograph comprising the thermal conductivity detector according to claim 12, wherein the first and second beam each have an electrode at the second end respectively.

* * * * *